United States Patent [19]
Okuno et al.

[11] Patent Number: 5,735,258
[45] Date of Patent: Apr. 7, 1998

[54] CUTTING MACHINE

[75] Inventors: Kiyohito Okuno; Sadahiko Itoh; Hisashi Horii, all of Ohtsu, Japan

[73] Assignee: MEMC Electronic Materials, Inc., St. Peters, Mo.

[21] Appl. No.: 717,092

[22] Filed: Sep. 20, 1996

[30] Foreign Application Priority Data

Sep. 22, 1995 [JP] Japan .................. 7-269504

[51] Int. Cl.⁶ .................................................. B28D 1/06
[52] U.S. Cl. ........................... 125/16.02; 125/16.03; 125/13.03; 125/19; 125/21
[58] Field of Search .................. 125/16.02, 16.03, 125/13.03, 19, 16.04, 16.01, 21; 451/387, 396

[56] References Cited

U.S. PATENT DOCUMENTS

| | | | |
|---|---|---|---|
| 4,727,852 | 3/1988 | Schmid et al. | 125/16 R |
| 5,080,085 | 1/1992 | Lovato | 125/21 |
| 5,269,285 | 12/1993 | Toyama et al. | 125/16.02 |

FOREIGN PATENT DOCUMENTS

| | | | |
|---|---|---|---|
| 112754 | 8/1980 | Japan | 125/21 |
| 2-152764 | 6/1990 | Japan | 27/6 |
| 6-35107 | 5/1994 | Japan | 27/6 |

*Primary Examiner*—Robert A. Rose
*Assistant Examiner*—George Nguyen
*Attorney, Agent, or Firm*—Senniger, Powers, Leavitt & Roedel

[57] ABSTRACT

A cutting machine by wires includes: groove rollers; wires moving by being tensioned by guide grooves of the groove rollers; and a holding mechanism for supporting a work piece for movement linearly into contact with the wires; wherein the holding mechanism is constituted so as to pivot the work piece.

12 Claims, 6 Drawing Sheets

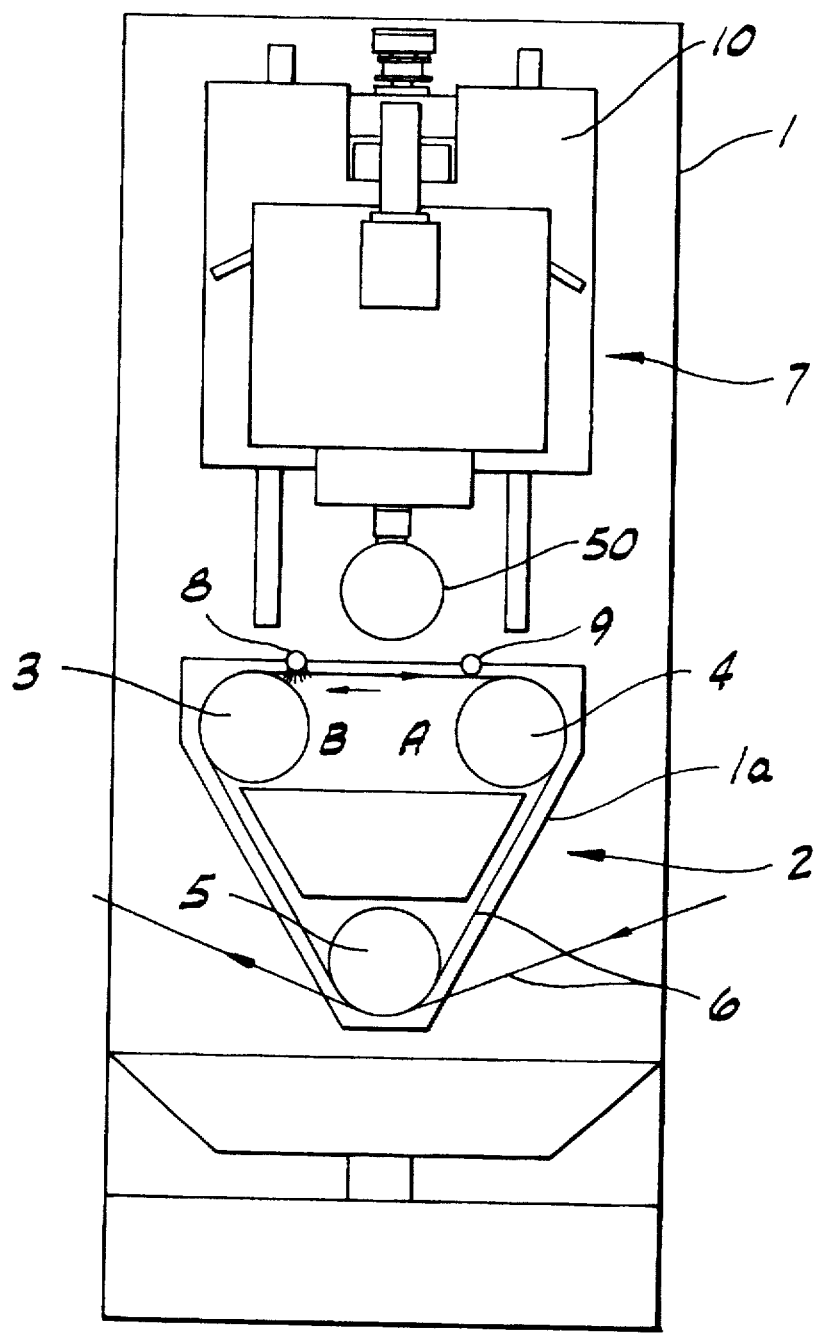

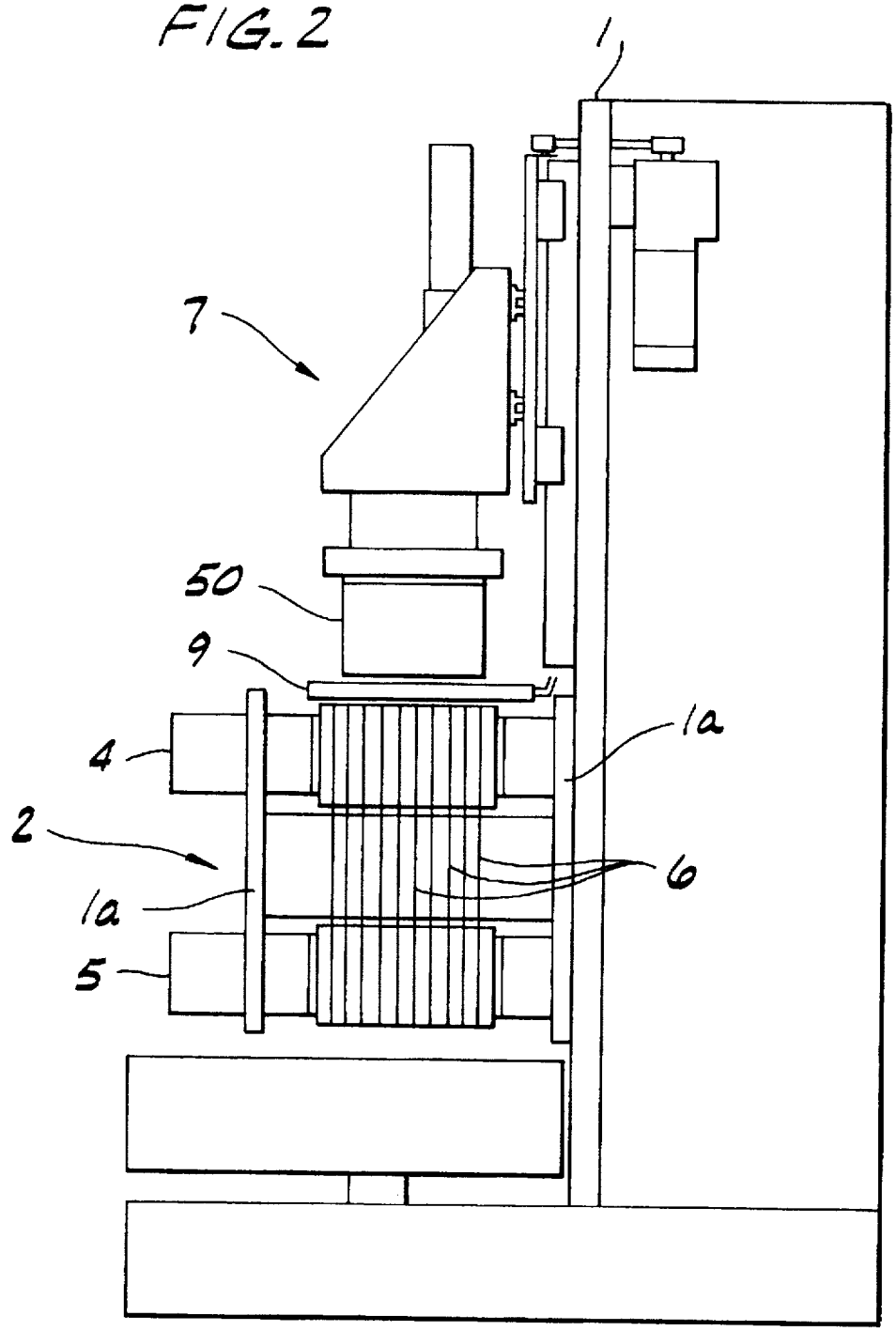

CUTTING MACHINE

BACKGROUND OF THE INVENTION

This invention relates to a cutting machine to cut blocks of ceramics, glass, silicon and others into slices.

A cutting machine slices blocks of ceramics, glass, silicon and so on into a plurality of slices. Such a cutting machine generally has: rollers which have guide grooves and which are pivotally mounted on a movable frame; a plurality of wires mounted on the rollers and received in the guide grooves; a work piece holder for holding a work piece in a predetermined position; and an ascending and descending device for bringing the work piece into contact with the wires.

In the aforementioned cutting machine, the work piece is cut by the wires as the work piece is moved linearly into the wires.

When a cylindrical work piece is moved along a line perpendicular to its longitudinal axis into the wires for slicing the work piece, the length of a wire contacting the work piece in the middle of cutting is substantially different from that in the beginning or at the end of cutting. Because the contact length of the wire with the work piece is long in the middle of cutting, supply of working liquid such as cooling liquid and abrasive liquid and discharge of particulate matter are relatively decreased, thereby deteriorating cutting conditions.

The diameters of work pieces (including specifically monocrystalline silicon ingots grown to form semiconductor wafers) have been increasing to the extent that the aforementioned cutting machine is unable to satisfactorily cut such large work pieces.

To solve the aforementioned problems, Japanese Patent Publication 6-35107 discloses a cutting machine. The cutting machine has a pivotal member and a pair of groove rollers for stretching a wire, the rollers being pivotally mounted on the pivotal member. The length of wire contacting a work piece can be adjusted by pivoting the pivotal member back and forth through a predetermined angle.

However, the aforementioned cutting machine has the following problems.

Pivoting the rollers carrying the wire causes the length and tension of the wire to be changed on the side from which the wire is released to the rollers and on the side where the wire is taken up from the rollers every time the rollers are pivoted. Accordingly, adjusting means having a number of take up wheels is required to make the necessary adjustment. This makes the structure of the cutting machine complex and substantially increases its size.

Further, it is very difficult to mount the wire with tension on the take up wheels and the groove rollers.

Furthermore, it is difficult to accelerate the speed of the work because the length of wire between the take up wheels is constantly changing.

SUMMARY OF THE INVENTION

The present invention aims to provide an improved wire cutting machine. The overall size of the cutting machine is relatively small, a wire can be easily mounted with tension, and the cutting machine readily permits acceleration of wire speed.

According to the present invention, there is provided a wire cutting machine comprising: groove rollers; wires tensioned in guide grooves of the groove rollers; and a holding mechanism for supporting a work piece for linear movement into contact with the wires; wherein the holding mechanism is constructed so as to pivot.

The holding mechanism preferably includes: a movable frame mounted on a framework so as to move freely; an arc guide formed on the movable frame; a movable supporting member mounted on the arc guide so as to move freely; and a driving mechanism to pivot the movable supporting member.

The driving mechanism preferably includes: a pinion mounted on an output axis of a reversible rotation member; an engaging portion combined with the movable supporting member; and a rack engaged with the pinion.

BRIEF DESCRIPTION OF THE DRAWINGS

FIG. 1 is a schematic front elevational view showing an embodiment of a cutting machine of the present invention.

FIG. 2 is a schematic side elevational view of FIG. 1.

FIGS. 6-1 through 6-3 are schematic views showing the relative orientations of wires and a work piece during a cutting operation.

DETAILED DESCRIPTION OF THE PREFERRED EMBODIMENT

Figure 3:
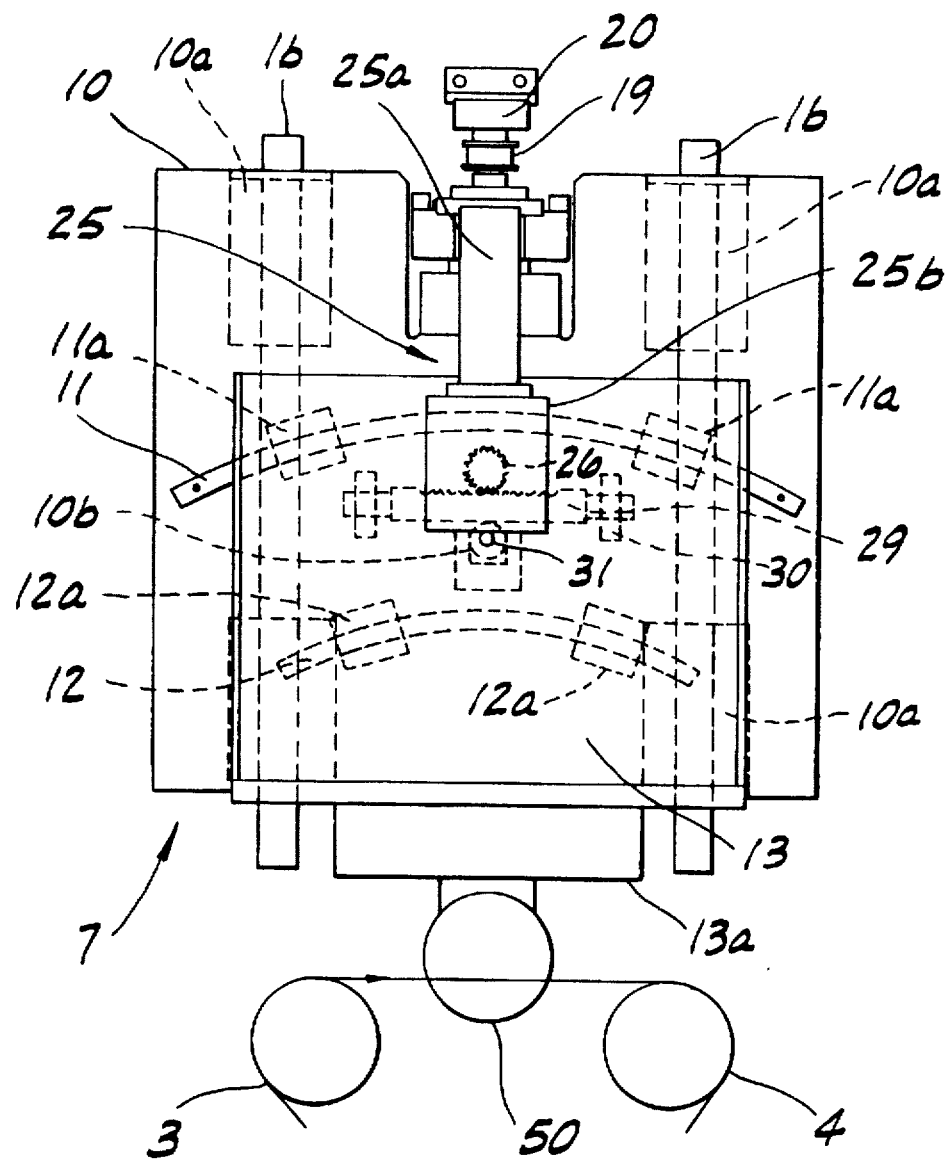
FIG. 3 is an enlarged front elevational view of a holding mechanism portion of the cutting machine of FIG. 1.

Referring to the drawings, a cutting machine includes three rollers 3, 4, and 5 having a plurality of grooves therein and rotatably mounted in parallel to one another on a framework 1; a cutting mechanism 2 including wires 6 wound around the rollers 3, 4, and 5; a holding mechanism 7 for supporting a work piece of ceramics, glass, silicon, etc., which is mounted on the framework 1 so as to ascend and descend perpendicularly and contact a work piece 50 to the wire; and nozzles 8 and 9 for supplying a working liquid such as a cooling liquid and an abrasive liquid in which a particulate abrasives and a cooling liquid are mixed with each other. The nozzles 8, 9 are attached to the machine so as to be located above the wires.

The aforementioned rollers 3, 4, and 5 are arranged in the form of an inverted triangle and pivotally mounted on a frame 1a which is fixed to the framework 1.

The wire 6 is wound around a drum (not shown) located to the side of cutting mechanism 2. The wire 6 passes from the drum, around the rollers 3, 4, and 5 to another drum located on the other side of the cutting mechanism 2 in the direction indicated by the arrowheads on the wire in FIG. 1.

The nozzles 8, 9 are connected to a pump for transmitting a liquid by a tube (not shown) which supplies a liquid and has a solenoid valve.

Figure 4:
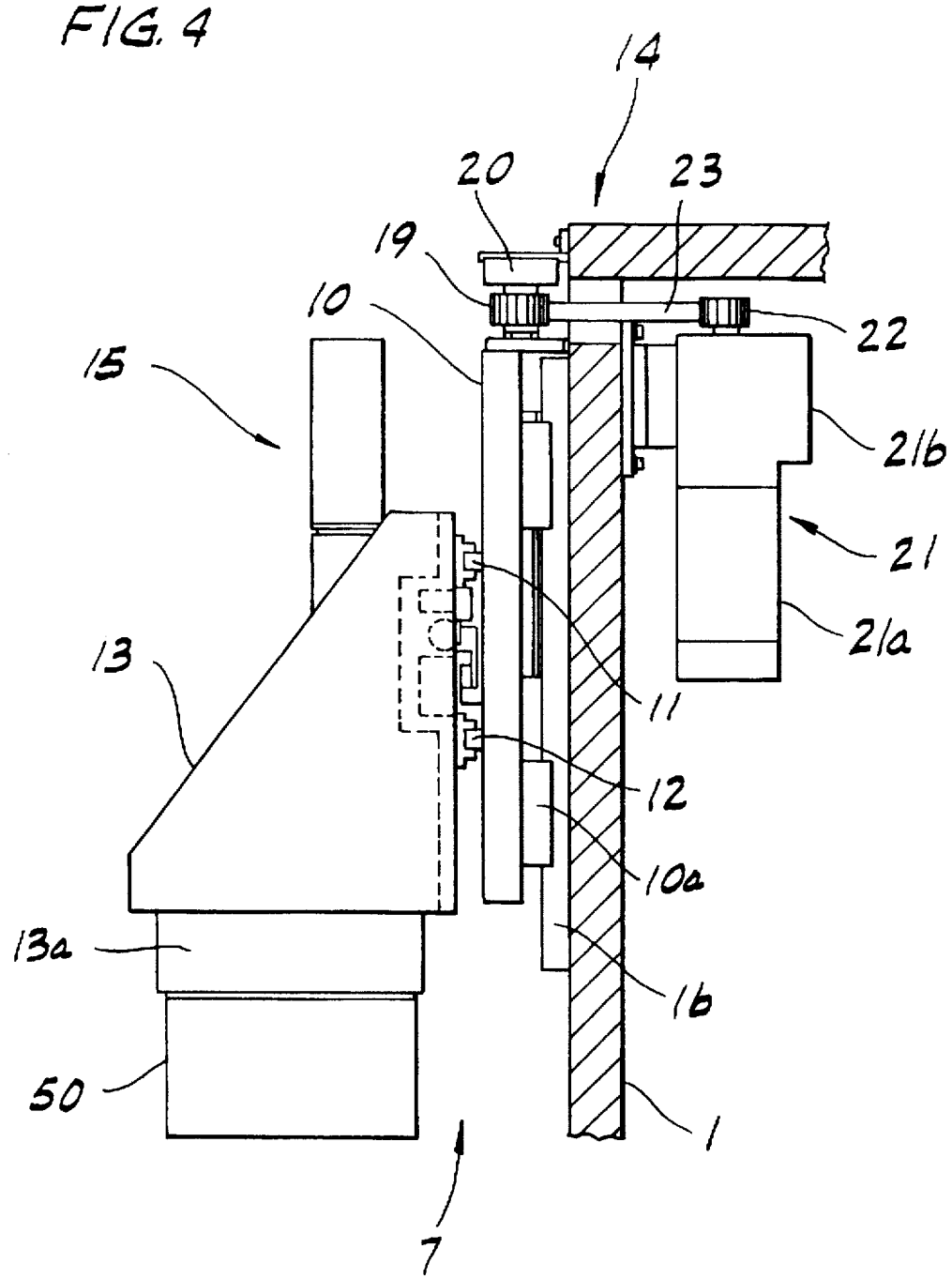
FIG. 4 is a fragmentary side elevational view of the holding mechanism of FIG. 3 shown partially in section to reveal internal construction.
Figure 5:
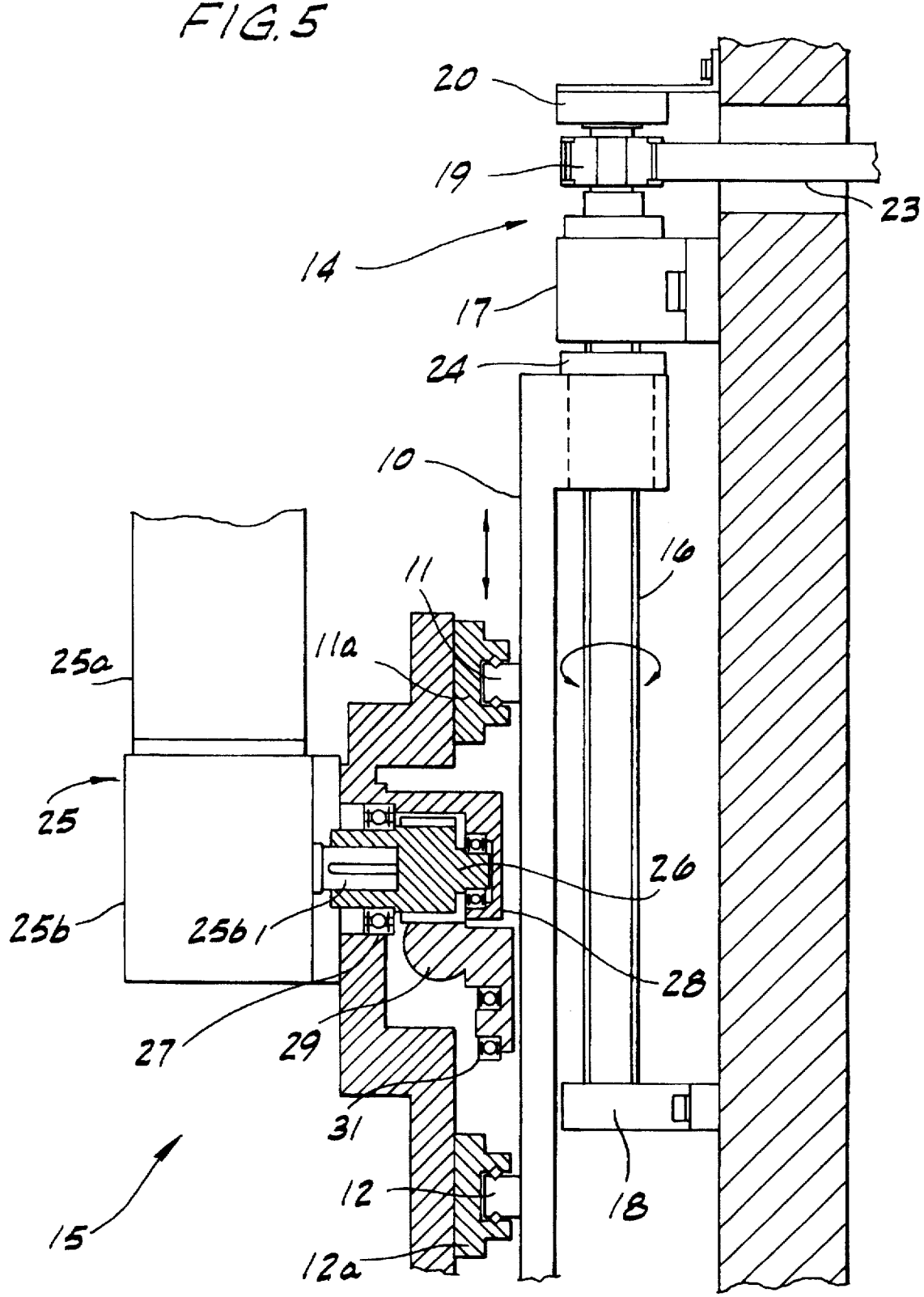
FIG. 5 is a further enlarged, fragmentary view of the holding mechanism of FIG. 4 with additional parts shown in section.

In the aforementioned holding mechanism 7, bearing portions 10a are movably mounted on guides 1b of the framework 1 as shown in FIGS. 3, 4, and 5. The holding mechanism 7 includes a movable frame 10 which is capable of moving up and down in a vertical direction, and slide members 11a and 12a. Guides 11 and 12 (commercial products produced by THK) are fixed to the movable frame 10, and a movable supporting member 13 is fixed to the slide members 11a and 12a. A driver 14 actuates movement of the movable frame 10, and a driving mechanism 15 is operable to pivot the movable supporting member 13 in both a clockwise and counterclockwise direction.

The centers of rotation of the arcs defined by the shape of each of the aforementioned guides 11, 12 coincide with each other and with the central longitudinal axis of the work piece 50.

It is envisioned that a guide (not shown) composed of an arcuate guideway having a dovetail groove and a movable bearing engaged in the dovetail groove may be used instead of the respective guides 11 and 12.

The movable supporting member 13 is provided with a base member 13a for use in securing the work piece 50 to the movable support member.

At one end of the driver 14, there is a sprocket wheel 19 having gear teeth (FIG. 5). The driver 14 includes a lead screw 16 mounted for rotation on the framework 1 by means of bearings 17 and 18 so as to be perpendicular to the framework 1. An electromagnetic brake 20 is fixed to the upper end of the lead screw 16. A reversible means 21 has a sprocket wheel 22 with gear teeth fixed to an output shaft of the reversible means 21. The reversible means includes a motor 21a and a reduction gear 21b both of which are mounted on the framework 1, and a chain 23 mounted with tension on the sprocket wheels 19 and 22. Thus, rotation of the lead screw 16 is selectively driven by operation of the reversible means 21.

The lead screw 16 is attached to the movable frame 10 by a ball-bearing assembly 24. The movable frame 10 may be selectively moved up and down along a guide 1b by rotation of the lead screw. The electromagnetic brake 20 is operable with the halt of the reversible means 21 to substantially simultaneously stop the rotation of the shaft 16, thereby precisely fixing the movable frame 10 in position.

Instead of the lead screw 16 and the ball-bearing assembly 24, a screwed shaft and a nut, or other linear actuator (not shown) may be used.

The driving mechanism 15 is operable to selectively pivot the movable supporting member 13. The driving mechanism comprises a reversible rotation mechanism 25 having a motor 25a mounted on the movable supporting member 13 and a reduction gear 25b (FIGS. 3 and 4). A pinion 26 is rotatably mounted on the movable supporting member 13 by bearings 27 and 28 and mounted on an output shaft 25b1 of the reduction gear 25b. A rack 29 is connected at each of its ends to the movable supporting member 13 by respective bearings 30. The bearings 30 permit lateral motion of the rack 29 relative to movable supporting member 13.

At a center portion of the rack 29, there is provided a bearing 31 on which the rack may pivot. The bearing 31 is received in a pocket 10b of the movable frame 10 which holds the bearing and rack 29 from moving horizontally relative to the frame, but permits the rack to pivot on the bearing with respect to the frame.

When the pinion 26 is rotated by the reversible rotation mechanism 25, the pinion 26 tries to move the rack 29 in a horizontal direction. However, the rack 29 cannot move horizontally because the rack 29 is connected to the movable frame 10 by reception of the bearing 31 in the pocket 10b. Accordingly, the pinion 26 moves on the rack 29.

Figures 1, 6:
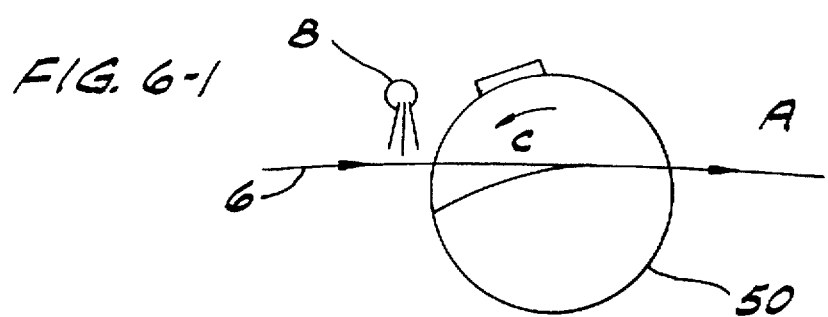
Figures 2, 6:
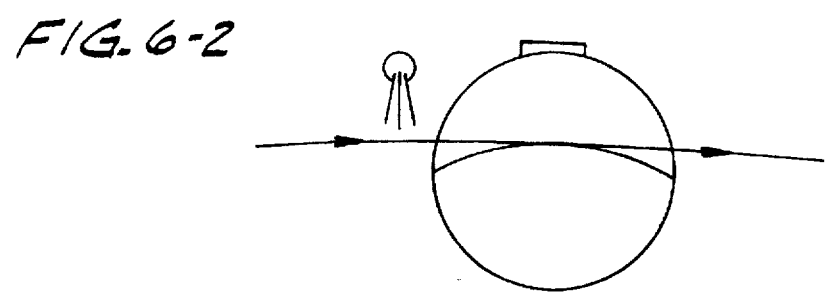
Figures 3, 6:
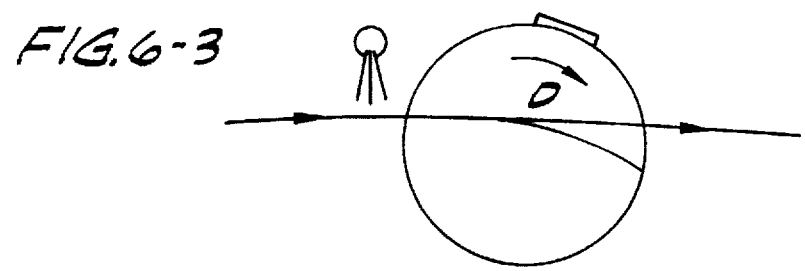

Thus, the movable supporting member 13, to which the pinion 26 and rotation mechanism 25 are attached, moves along the respective arcuate guides 11 and 12. The work piece 50 held on the base member 13a of the movable supporting member 13 is rotated continuously back and forth through a predetermined angle with respect to the wires 6, as shown in FIG. 6.

The operation of the cutting machine of the present invention is hereinbelow described.

First, the work piece 50 is fixed to the base member 13a of the movable supporting member 13 in a conventional manner. The wires 6 are moved in a direction shown at an arrow A by rotating rollers 3, 4, and 5 of the cutting mechanism 2 at a predetermined speed, and simultaneously, a working liquid is supplied to the wire 6 by operating a pump of a liquid supply mechanism (not shown) connected to nozzles 8 and 9 for supplying a liquid.

The shaft 16 is rotated by controlled operation of the driver 14 to move the movable frame 10, and the work piece 50 carried by the movable frame, at a predetermined speed into the wires 6.

Simultaneously, the pinion 26 is rotated forward and backward by the reversible rotation mechanism 25 of the driving mechanism 15. The work piece 50 is turned back and forth (in a direction C or D shown in FIG. 6-1 and 6-3, respectively) through a predetermined angle.

In this way, the length of the wire 6 contacting the work piece 50 can be maintained substantially more constant as the work piece is cut. Therefore, a work piece having a large diameter can easily be cut with the cutting machine of the present invention.

In the aforementioned embodiment, the wires 6 released from a drum (not shown) are moved in direction A and taken up by the other drum (not shown). Then, the drums are rotated in the opposite direction so as to move the wires 6 in direction B. The speed of the wires 6 may be changed depending on a direction in which the wires move, as well understood to those of ordinary skill in the art.

In the aforementioned embodiment, the work piece 50 was swung back and forth in an oscillating motion from the beginning to the end of a cutting process. However, the work piece 50 may be swung back and forth only in the middle of the cutting process without departing from the scope of the present invention.

In a cutting machine of the present invention, a support mechanism is pivoted through a predetermined angle about an axis substantially coincident with the longitudinal axis of the work piece. Therefore, the size of the whole apparatus can be made small, and wires can be easily mounted with tension. Further, a speed of the wires can be increased since the construction of a cutting mechanism by wires is not complex. Furthermore, the length of the wire 6 contacting the work piece 50 can be adjusted during the cut. Therefore, the work piece having a large diameter can easily be cut.

In the preferred embodiment, a holding mechanism comprises: a movable frame mounted on a machine so as to move freely; an arc guide formed on the movable frame; a moveable supporting member mounted on the arc guide so as to move freely; and a driving mechanism to move the movable supporting member through a predetermined angle. The driving mechanism preferably comprises: a pinion mounted on an output axis of a reversible rotation member; an engaging portion combined with a movable supporting member; and a rack engaged with the pinion. A work piece can be smoothly swung back and forth through a predetermined angle with respect to the wires by the aforementioned driving mechanism.

What is claimed is:

1. A cutting machine for cutting a workpiece, the cutting machine comprising:

a framework;

a cutting mechanism;

a holding mechanism constructed for holding the work piece as the work piece is cut by the cutting mechanism, the holding mechanism and cutting mechanism being arranged for relative movement to bring the work piece into contact with the cutting mechanism for cutting the work piece;

the holding mechanism being mounted on the framework for pivoting motion with respect to the framework thereby to pivot the work piece relative to the cutting mechanism as the workpiece is cut by the cutting mechanism, the holding mechanism being mounted for pivoting the work piece about a longitudinal axis of the work piece, said pivoting motion comprising a rocking, reciprocating motion.

2. A cutting machine as set forth in claim 1 wherein the cutting mechanism comprises a cutting element for contacting the work piece to cut the work piece, the holding mechanism being controlled to pivot for maintaining the length of the cutting element contacting the work piece substantially constant as the work piece is cut.

3. A cutting machine as set forth in claim 2 wherein the cutting mechanism further comprises rollers and the cutting element comprises wire extending around the rollers, the wire including a reach between rollers for cutting the work piece.

4. A cutting machine as set forth in claim 1, wherein the holding mechanism comprises:

a movable frame mounted on the framework for movement relative to the framework and cutting mechanism to move the work piece into the cutting mechanism;

an arcuate guide on the movable frame;

a movable supporting member mounted on the arcuate guide for movement in an arc relative to the movable frame; and a driving mechanism to move the movable supporting member back and forth along the arc for pivoting the work piece relative to the cutting mechanism.

5. A cutting machine as set forth in claim 4 wherein the driving mechanism comprises:

a reversible rotation mechanism operatively connected to the supporting member, the reversible rotation mechanism including a pinion;

a rack associated with the movable frame and engaged with the pinion whereby rotation of the pinion moves the supporting member relative to the movable frame on the arcuate guide.

6. A cutting machine as set forth in claim 5 wherein the rack is held from translational movement with respect to the movable frame but is permitted to pivot with respect to the movable frame.

7. A cutting machine for cutting a workpiece, the cutting machine comprising:

a framework;

a cutting mechanism;

a holding mechanism constructed for holding the work piece as the work piece is cut by the cutting mechanism, the holding mechanism and cutting mechanism being arranged for relative movement to bring the work piece into contact with the cutting mechanism for cutting the work piece;

the holding mechanism being mounted on the framework for pivoting motion with respect to the framework thereby to pivot the work piece relative to the cutting mechanism as the workpiece is cut by the cutting mechanism;

the holding mechanism comprising;

a movable frame mounted on the framework for movement relative to the framework and cutting mechanism to move the work piece into the cutting mechanism.

an arcuate guide on the movable frame, a movable supporting member mounted on the arcuate guide for movement in an arc relative to the movable frame, and a driving mechanism to move the movable supporting member back and forth along the arc for pivoting the work piece relative to the cutting mechanism.

8. A cutting machine as set forth in claim 7 wherein the holding mechanism is mounted for pivoting the work piece about a longitudinal axis of the work piece.

9. A cutting machine as set forth in claim 7 wherein the cutting mechanism comprises a cutting element for contacting the work piece to cut the work piece, the holding mechanism being controlled to pivot for maintaining the length of the cutting element contacting the work piece substantially constant as the work piece is cut.

10. A cutting machine as set forth in claim 9 wherein the cutting mechanism further comprises rollers and the cutting element comprises wire extending around the rollers, the wire including a reach between rollers for cutting the work piece.

11. A cutting machine as set forth in claim 7 wherein the driving mechanism comprises:

a reversible rotation mechanism operatively connected to the supporting member, the reversible rotation mechanism including a pinion;

a rack associated with the movable frame and engaged with the pinion whereby rotation of the pinion moves the supporting member relative to the movable frame on the arcuate guide.

12. A cutting machine as set forth in claim 11 wherein the rack is held from translational movement with respect to the movable frame but is permitted to pivot with respect to the movable frame.

* * * * *